(12) United States Patent
Henkelmann et al.

(10) Patent No.: US 8,598,060 B2
(45) Date of Patent: *Dec. 3, 2013

(54) METHOD OF REGENERATING RUTHENIUM CATALYSTS FOR THE RING HYDROGENATION OF PHTHALATES

(75) Inventors: Jochem Henkelmann, Mannheim (DE); Michael Becker, Offenburg (DE); Felix Richter, Ludwigshafen (DE); Thomas Schäfer, Mannheim (DE)

(73) Assignee: BASF SE (DE)

( * ) Notice: Subject to any disclaimer, the term of this patent is extended or adjusted under 35 U.S.C. 154(b) by 282 days.

This patent is subject to a terminal disclaimer.

(21) Appl. No.: 12/375,598

(22) PCT Filed: Jul. 25, 2007

(86) PCT No.: PCT/EP2007/057651
§ 371 (c)(1),
(2), (4) Date: Jan. 29, 2009

(87) PCT Pub. No.: WO2008/015135
PCT Pub. Date: Feb. 7, 2008

(65) Prior Publication Data
US 2009/0305869 A1 Dec. 10, 2009

(30) Foreign Application Priority Data
Jul. 31, 2006 (EP) ..................... 06118205

(51) Int. Cl.
*B01J 20/34* (2006.01)
(52) U.S. Cl.
USPC ........................................... 502/34
(58) Field of Classification Search
None
See application file for complete search history.

(56) References Cited

U.S. PATENT DOCUMENTS

| | | | |
|---|---|---|---|
| 2,757,128 A | 7/1956 | Hemminger | |
| 3,245,919 A | 4/1966 | Gring et al. | |
| 3,851,004 A | 11/1974 | Yang | |
| 5,612,009 A | 3/1997 | Fetzer et al. | |
| 5,817,589 A * | 10/1998 | de Agudelo et al. | 502/53 |
| 5,877,364 A | 3/1999 | Hernandez et al. | |
| 5,942,645 A | 8/1999 | Rütter et al. | |
| 6,521,791 B1 * | 2/2003 | Welp et al. | 564/423 |
| 6,524,993 B2 * | 2/2003 | Yamaguchi et al. | 502/328 |

(Continued)

FOREIGN PATENT DOCUMENTS

| | | |
|---|---|---|
| DE | 19604791 | 8/1997 |
| DE | 19634880 | 10/1997 |

(Continued)

OTHER PUBLICATIONS

J. Lemaitre et al. "Characterization of Heterogeneous Catalysts", Editor: Francis Delanney, Marcel Dekker, New York 1984, pp. 310-324.

Robert Schaffer, "The Development of a Clinical Reference Method for Glucose in Serum," Pure & Appl. Chem., vol. 45, pp. 75-79 (1976).

(Continued)

*Primary Examiner* — Melvin C Mayes
*Assistant Examiner* — Stefanie Cohen
(74) *Attorney, Agent, or Firm* — Novak Druce Connolly Bove + Quigg LLP

(57) ABSTRACT

The present invention relates to a method of regenerating a ruthenium catalyst for the hydrogenation of phthalates, which comprises flushing the catalyst with inert gas in a regeneration step until the original activity or part of the original activity has been attained.

19 Claims, 1 Drawing Sheet

(56) References Cited

U.S. PATENT DOCUMENTS

| | | | |
|---|---|---|---|
| 6,962,947 B2 * | 11/2005 | Wright et al. | 518/709 |
| 7,208,545 B1 | 4/2007 | Brunner et al. | |
| 7,355,084 B2 | 4/2008 | Böttcher et al. | |
| 2001/0000035 A1 | 3/2001 | Ruhl et al. | |
| 2004/0199033 A1 * | 10/2004 | Bottcher et al. | 585/267 |

FOREIGN PATENT DOCUMENTS

| | | | |
|---|---|---|---|
| DE | 19624485 | | 1/1998 |
| DE | 19917051 | * | 2/2002 |
| DE | 10128242 | | 12/2002 |
| DE | 10200502920 | * | 12/2006 |
| DE | 102005029200 | | 12/2006 |
| EP | 0243894 | | 11/1987 |
| EP | 0913194 | | 5/1999 |
| EP | 1169285 | | 1/2002 |
| EP | 0814098 | | 4/2004 |
| JP | 01159059 | | 6/1989 |
| JP | 03068453 | | 3/1991 |
| JP | 2000051701 | | 2/2000 |
| KR | 1020087001732 | | 3/2008 |
| WO | WO-93/04774 | | 3/1993 |
| WO | WO-00/63142 | | 12/2000 |
| WO | WO-00/78704 | | 12/2000 |

OTHER PUBLICATIONS

Fundamentals of Industrial Catalytic Processes, R. J. Farrauto, C.H. Bartholomew, First Edition 1997, pp. 16 to 17, 57 to 62, 88 to 91, and 110 to 111.

Oberlander, R.K. "Aluminas for Catalysts—their preparations and properties," in Applied Industrial Catalysis, e.g. D.E. Leach, Academic Press, vol. 3, Chapter 4, 1984.

"Adsorbent and Catalytic Aluminas," Ullmann's Encyclopedia of Industrial Chemistry, 5th Ed., vol. A1, pp. 588 to 590; VCH 1985.

O.W. Flörke et al., "Silica" in Ullmann's Encylopedia of Industrial Chemistry, $6^{th}$ edition, vol. 32, pp. 273-359, 2003.

F. J. Bröcker, "Hydrierung and Dehydrierung, katalytische," Ullmanns Enzyklopädie der Technischen Chemie, 4th edition, vol. 13, pp. 135-147, 1962.

P.N. Rylander, "Hydrogenation and Dehydrogenation" in Ullmann's Encyclopedia of Industrial Chemistry, 5th edition, vol. A13, pp. 487-497, 1996.

DIN 66131—Determination of the specific surface area of solids by gas adsorption using the BET method; ISO 9277, 1995.

DIN 66133—Determination of pore volume distribution and specific surface area of solids by mercury intrusion, Jun. 1993.

International Preliminary Report on Patentability for International Application No. PCT/EP2007/057651, mailed Mar. 19, 2009.

International Search Report for International Application No. PCT/EP2007/057651, mailed Jan. 22, 2008.

* cited by examiner

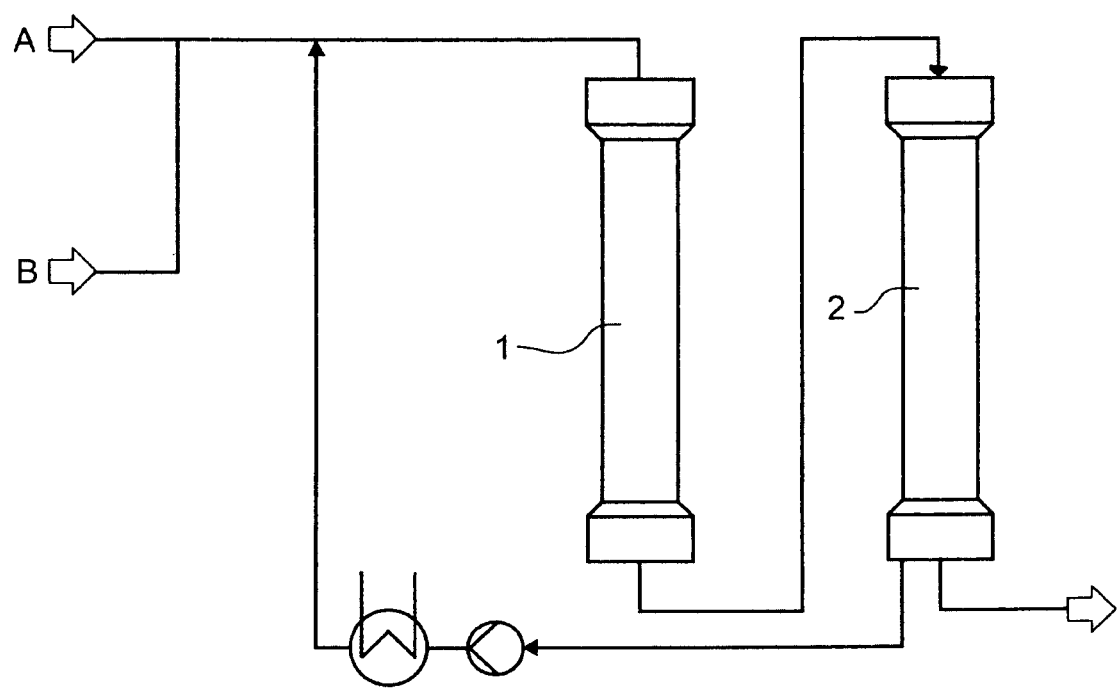

METHOD OF REGENERATING RUTHENIUM CATALYSTS FOR THE RING HYDROGENATION OF PHTHALATES

CROSS REFERENCE TO RELATED APPLICATIONS

This application is a national phase of PCT/EP2007/057651, filed on Jul. 25, 2007, which claims priority to EP 06118205.1, filed on Jul. 31, 2006, the entire contents of which are incorporated herein by reference in their entireties.

The present invention relates to a method of regenerating a catalyst which is used, in particular, for the hydrogenation of phthalates to the corresponding cyclohexane-dicarboxylic acid derivatives.

A process for preparing selected cyclohexane-1,3- and cyclohexane-1,4-dicarboxylic acids is disclosed in WO 00/78704. These compounds are highly suitable as plasticizers. Particular mention may be made of diisononyl cyclohexane-1,4-dicarboxylate.

A particularly useful catalyst which can be used in the hydrogenation of aromatic compounds is disclosed in DE 196 24 485 A1. The catalyst comprises, as active metal, either ruthenium alone or ruthenium together with at least one metal of transition group I, VII or VIII of the Periodic Table (CAS version) in an amount of from 0.01 to 30% by weight, based on the total weight of the catalyst, applied to a support. From 10 to 50% of the pore volume of the support is formed by macropores having a pore diameter in the range from 50 nm to 10 000 nm and from 50 to 90% of the pore volume of the support is formed by mesopores having a pore diameter in the range from 2 to 50 nm, with the sum of the pore volumes being 100%. Supports used are activated carbon, silicon carbide, aluminum oxide, silicon dioxide, titanium dioxide, zirconium dioxide, magnesium dioxide, zinc oxide or a mixture of two or more thereof.

Further particularly useful catalysts for the hydrogenation of aromatic compounds are disclosed in EP-A 1 169 285. In one embodiment (catalyst 1), the catalyst comprises at least one metal of transition group VIII of the Periodic Table (CAS version) applied to a support, with the support having macropores and the catalyst comprises, as active metal, at least one metal of transition group VIII of the Periodic Table, either alone or together with at least one metal of transition group I or VII of the Periodic Table, applied to a support, with the support having a mean pore diameter of at least 50 nm and a BET surface area of not more than 30 m²/g and the amount of active metal being from 0.01 to 30% by weight, based on the total weight of the catalyst. In a further embodiment (catalyst 2), the catalyst comprises, as active metal, at least one metal of transition group VIII of the Periodic Table, either alone or together with at least one metal of transition group I or VII of the Periodic Table in an amount of from 0.01 to 30% by weight, based on the total weight of the catalyst, applied to a support, with from 10 to 50% of the pore volume of the support being formed by macropores having a pore diameter in the range from 50 nm to 10 000 nm and from 50 to 90% of the pore volume of the support being formed by mesopores having a pore diameter in the range from 50 nm to 10 000 nm and from 50 to 90% of the pore volume of the support being formed by mesopores having a pore diameter in the range from 2 to 50 nm, with the sum of the proportions of the pore volumes being 100%. Supports used are activated carbon, silicon carbide, aluminum oxide, silicon dioxide, titanium dioxide, zirconium dioxide, magnesium dioxide, zinc oxide or a mixture of two or more thereof, preferably aluminum oxide.

Finally, a further particularly useful catalyst is disclosed in the patent application DE 102 005 029 200. This is a coated catalyst comprising, as active metal, either ruthenium alone or ruthenium together with at least one further metal of transition group IB, VIIB or VIII of the Periodic Table of the Elements (CAS version) applied to a support comprising silicon dioxide as support material, wherein the amount of active metal is <1% by weight, based on the total weight of the catalyst, and at least 60% by weight of the active metal is present in the shell of the catalyst to a penetration depth of 200 μm, determined by means of SEM-EPMA (EXDS).

The maintenance of the catalyst activity over a very long period of time is of great economic importance for industrial processes.

A decrease in the catalytic activity is usually caused by various physical and chemical effects on the catalyst, for example by blocking of the catalytically active sites or by loss of catalytically active sites as a result of thermal, mechanical or chemical processes. For example, catalyst deactivation or aging in general can be caused by sintering of the catalytically active sites, by loss of (noble) metal, as a result of deposits or by poisoning of the active sites. There are many aging/deactivation mechanisms.

Conventionally, the deactivated catalyst has to be removed from the reactor for regeneration. The reactor is then down, or operation is resumed after installation of another catalyst. In either case, this leads to significant costs. The U.S. Pat. No. 3,851,004 and U.S. Pat. No. 2,757,128 disclose processes for the hydrogenation of, inter alia, olefins in hydrocarbon starting materials and the regeneration of the catalysts by means of hydrogen.

DE 196 34 880 C2 discloses a process for the simultaneous selective hydrogenation of diolefins and nitriles from a hydrocarbon starting material. In this process, the catalyst is, after its diolefin hydrogenation activity has dropped to less than 50% of the initial activity, flushed with an inert gas to remove traces of the hydrocarbon from the catalyst and to produce a flushed catalyst and this is flushed with hydrogen in a subsequent regeneration step. This produces a regenerated catalyst whose diolefin hydrogenation activity is once again at least 80% of the initial value.

Deactivation is likewise observed in the hydrogenation of phthalates using the ruthenium catalysts described, and this deactivation has not yet been able to be overcome in a simple way.

It is an object of the present invention to provide a method of regenerating a ruthenium catalyst used in the hydrogenation of phthalates. This should be simple to implement in terms of apparatus and be inexpensive to carry out. In particular, multiple and complete regeneration of the catalyst is sure to be able to be achieved thereby.

The above object is achieved by a method of regenerating a ruthenium catalyst for the hydrogenation of phthalates, which comprises flushing the catalyst with inert gas in a regeneration step until the original activity or part of the original activity has been attained.

This regeneration firstly results in higher conversions due to an increased catalyst activity, and, secondly, the catalyst operating lives in production operation are significantly increased by means of the method of the invention.

The method of the invention is particularly suitable for regeneration of Ru catalysts which are described in the patent applications EP-A 0 814 098, EP-A 1 169 285 and DE 102 005 029 200 are used in the processes disclosed there. These catalysts and processes are described below.

In all of the present patent application, the groups of the Periodic Table are designated according to the CAS version.

Preferred Catalysts
EP-A 0 814 098

The catalysts described below are designated as "catalyst variant I" in the present patent application.

As active metals, it is in principle possible to use all metals of transition group VIII of the Periodic Table. Preference is given to using platinum, rhodium, palladium, cobalt, nickel or ruthenium or a mixture of two or more thereof as active metals, with particular preference being given to using ruthenium as active metal.

The terms "macropores" and "mesopores" are, for the purposes of the present invention, used in accordance with the definition in *Pure Appl. Chem.*, 45, p. 79 (1976), namely pores whose diameter is above 50 nm (macropores) or whose diameter is in the range from 2 nm to 50 nm (mesopores). "Micropores" are likewise defined in the references cited above and denote pores having a diameter of <2 nm.

The active metal content is generally from about 0.01 to about 30% by weight, preferably from about 0.01 to about 5% by weight and in particular from about 0.1 to about 5% by weight, in each case based on the total weight of the catalyst used.

The total metal surface area in catalyst variant I is preferably from about 0.01 to about 10 $m^2/g$, more preferably from about 0.05 to about 5 $m^2/g$ and in particular from about 0.05 to about 3 $m^2/g$, of the catalyst. The metal surface area is determined by means of the chemisorption method described by J. Lemaitre et al. in "*Characterization of Heterogeneous Catalysts*", editor. Francis Delanney, Marcel Dekker, New York 1984, pp. 310-324.

In catalyst variant I, the ratio of the surface areas of the active metal/metals and the catalyst support is preferably less than about 0.05, with the lower limit being about 0.0005.

Catalyst variant I comprises a support material which is macroporous and has a mean pore diameter of at least about 50 nm, preferably at least about 100 nm, in particular at least about 500 nm, and whose BET surface area is not more than about 30 $m^2/g$, preferably not more than about 15 $m^2/g$, more preferably not more than about 10 $m^2/g$, in particular not more than about 5 $m^2/g$ and more preferably not more than about 3 $m^2/g$. The mean pore diameter of the support is preferably from about 100 nm to about 200 μm, more preferably from about 500 nm to about 50 μm. The BET surface area of the support is preferably from about 0.2 to about 15 $m^2/g$, more preferably from about 0.5 to about 10 $m^2/g$, in particular from about 0.5 to about 5 $m^2/g$ and more preferably from about 0.5 to about 3 $m^2/g$.

The surface area of the support is determined by the BET method by means of $N_2$ adsorption, in particular in accordance with DIN 66131. The determination of the mean pore diameter and the pore size distribution is carried out by means of Hg porosimetry, in particular in accordance with DIN 66133.

The pore size distribution of the support can preferably be approximately bimodal, with the pore diameter distribution having maxima at about 600 nm and about 20 μm in the bimodal distribution representing a specific embodiment of the invention.

Further preference is given to a support which has a surface area of 1.75 $m^2/g$ and has this bimodal distribution of the pore diameter. The pore volume of this preferred support is preferably about 0.53 ml/g.

As macroporous support material, it is possible to use, for example, macropore-comprising activated carbon, silicon carbide, aluminum oxide, silicon dioxide, titanium dioxide, zirconium dioxide, magnesium oxide, zinc oxide or mixtures of two or more thereof, with particular preference being given to using aluminum oxide and zirconium dioxide.

Corresponding catalyst supports and methods of producing them are disclosed in the following documents:

Fundamentals of Industrial Catalytic Processes, R. J. Farrauto, C. H. Bartholomew, First Edition 1997, pages 16, 17, 57 to 62, 88 to 91, 110 to 111; Oberlander, R. K., 1984 Aluminas for Catalysts, in Applied Industrial Catalysis, e.g. D. E. Leach, Academic Press, Vol. 3, Chapter 4; U.S. Pat. No. 3,245,919; WO 93/04774; EP-A 0 243 894; Ullmann's Encyclopedia of Industrial Chemistry, 5th Ed., Vol. AI, pp. 588 to 590; VCH 1985.

EP-A 1 169 285

The catalysts described below are designated as "catalyst variant II" in the present patent application. There are various subvariants of this variant II.

Subvariant 1

This catalyst corresponds to that described about under EP-A 0 814 089.

A description is also given of the subvariant 1a used according to the invention, which represents a preferred embodiment of subvariant 1. Support materials which can be used are ones which are macroporous and have a mean pore diameter of at least 0.1 μm, preferably at least 0.5 μm, and a surface area of not more than 15 $m^2/g$, preferably not more than 10 $m^2/g$, particularly preferably not more than 5 $m^2/g$, in particular not more than 3 $m^2/g$. The mean pore diameter of the support used there is preferably in the range from 0.1 to 200 μm, in particular from 0.5 to 50 μm. The surface area of the support is preferably from 0.2 to 15 $m^2/g$, particularly preferably from 0.5 to 10 $m^2/g$, in particular from 0.5 to 5 $m^2/g$, especially from 0.5 to 3 $m^2/g$, of the support. This catalyst, too, has the above-described bimodality of the pore diameter distribution with the analogous distributions and the correspondingly preferred pore volume. Further details regarding subvariant 1a may be found in DE-A 196 04 791.9 whose contents are fully incorporated by reference into the present patent application.

Subvariant 2

Subvariant 2 comprises one or more metals of transition group VIII of the Periodic Table as active component(s) on a support as defined herein. Ruthenium is preferably used as active component.

The total metal surface area on the catalyst is preferably from 0.01 to 10 $m^2/g$, particularly preferably from 0.05 to 5 $m^2/g$ and more preferably from 0.05 to 3 $m^2/g$, of the catalyst. The metal surface area was measured by the chemisorption method described in J. Lemaitre et al., "*Characterization of Heterogeneous Catalysts*", Editor: Francis Delanney, Marcel Dekker, New York (1984), pp. 310-324.

In subvariant 2, the ratio of the surface areas of the at least one active metal and the catalyst support is less than about 0.3, preferably less than about 0.1 and in particular about 0.05 or less, with the lower limit being about 0.0005.

The support materials which can be used in subvariant 2 have macropores and mesopores.

The supports which can be used have a pore distribution in which from about 5 to about 50%, preferably from about 10 to about 45%, more preferably from about 10 to about 30% and in particular from about 15 to about 25%, of the pore volume is formed by macropores having pore diameters in the range from about 50 nm to about 10 000 nm and from about 50 to about 95%, preferably from about 55 to about 90%, more preferably from about 70 to about 90% and in particular from about 75 to about 85%, of the pore volume is formed by mesopores having a pore diameter of from about 2 to about 50 nm, with the sum of the proportions of the pore volumes in each case being 100%.

The total pore volume of the supports used is from about 0.05 to 1.5 cm$^3$/g, preferably from 0.1 to 1.2 cm$^3$/g and in particular from about 0.3 to 1.0 cm$^3$/g. The mean pore diameter of the supports used according to the invention is from about 5 to 20 nm, preferably from about 8 to about 15 nm and in particular from about 9 to about 12 nm.

The surface area of the support is preferably from about 50 to about 500 m$^2$/g, more preferably from about 200 to about 350 m$^2$/g and in particular from about 250 to about 300 m$^2$/g, of the support.

The surface area of the support is determined by the BET method by means of $N_2$ adsorption, in particular in accordance with DIN 66131. The determination of the mean pore diameter and the size distribution is carried out by means of Hg porosimetry, in particular in accordance with DIN 66133.

Although it is in principle possible to use all support materials known in catalyst production, i.e. those which have the above-defined pore size distribution, preference is given to using activated carbon, silicon carbide, aluminum oxide, silicon dioxide, titanium dioxide, zirconium dioxide, magnesium oxide, zinc oxide and mixtures thereof, more preferably aluminum oxide and zirconium dioxide.
DE 102 005 029 200

The catalysts disclosed below are designated as catalyst variant III or "coated catalysts" in the present patent application.

The subject matter is a coated catalyst comprising, as active metal, either ruthenium alone or ruthenium together with at least one further metal of transition group IB, VIIB or VIII of the Periodic Table of the Elements (CAS version) applied to a support comprising silicon dioxide as support material.

In this coated catalyst, the amount of active metal is <1% by weight, preferably from 0.1 to 0.5% by weight, particularly preferably from 0.25 to 0.35% by weight, based on the total weight of the catalyst, and at least 60% by weight, particularly preferably 80% by weight, of the active metal, based on the total amount of active metal, is present in the shell of the catalyst to a penetration depth of 200 μm. The data given above are determined by means of SEM (scanning electron microscopy) EPMA (electron probe microanalysis)-EDXS (energy dispersive X-ray spectroscopy) and represent mean values. Further information regarding the above-described measurement methods and techniques are disclosed, for example, in "Spectroscopy in Catalysis" by J. W. Niemantsverdriet, VCH, 1995.

In the coated catalyst, the predominant amount of the active metal is present in the shell to a penetration depth of 200 μm, i.e. near the surface of the coated catalyst. In contrast, no active metal or only a very small amount of active metal is present in the interior (core) of the catalyst. It has surprisingly been found that the catalyst variant III has, despite the small amount of active metal, a very high activity in the hydrogenation of organic compounds comprising hydrogenatable groups, in particular in the hydrogenation of carbocyclic aromatic groups, at very good selectivities. In particular, the activity of catalyst variant III does not decrease over a long hydrogenation time.

Very particular preference is given to a coated catalyst in which no active metal can be detected in the interior of the catalyst, i.e. active metal is present only in the outer shell, for example in a zone to a penetration depth of from 100 to 200 μm.

In a further particularly preferred embodiment, active metal particles can be detected only in the outermost 200 μm, preferably 100 μm, very particularly preferably 50 μm (penetration depth), of the coated catalyst by means of (FEG)-TEM (field emission gun-transmission electron microscopy) with EDXS.

As active metal, it is possible to use either ruthenium alone or ruthenium together with at least one further metal of transition group IB, VIIB or VIII of the Periodic Table of the Elements (CAS version). Further active metals which are suitable in addition to ruthenium are, for example, platinum, rhodium, palladium, iridium, cobalt or nickel or a mixture of two or more thereof. Among the metals of transition groups IB and/or VIIB of the Periodic Table of the Elements which can likewise be used, suitable metals are, for example, copper and/or rhenium. Preference is given to using ruthenium alone as active metal or together with platinum or iridium in the coated catalyst; very particular preference is given to using ruthenium alone as active metal.

The coated catalyst displays the abovementioned very high activity at a low loading with active metal of <1% by weight, based on the total weight of the catalyst. The amount of active metal in the coated catalyst according to the invention is preferably from 0.1 to 0.5% by weight, particularly preferably from 0.25 to 0.35% by weight. It has been found that the penetration depth of the active metal into the support material is dependent on the loading of the catalyst variant III with active metal. Even at a loading of the catalyst variant III with 1% by weight or more, e.g. at a loading with 1.5% by weight, a significant amount of active metal is present in the interior of the catalyst, i.e. at a penetration depth of from 300 to 1000 μm, and this impairs the activity of the hydrogenation catalyst, in particular the activity over a long hydrogenation time, particularly in the case of fast reactions, with a deficiency of hydrogen being able to occur in the interior of the catalyst (core).

In the coated catalyst, at least 60% by weight of the active metal, based on the total amount of active metal, is present in the shell of the catalyst to a penetration depth of 200 μm. Preference is given to at least 80% by weight of the active metal in the coated catalyst, based on the total amount of active metal, being present in the shell of the catalyst to a penetration depth of 200 μm. Very particular preference is given to a coated catalyst in which no active metal can be detected in the interior of the catalyst, i.e. active metal is present only in the outermost shell, for example in a zone to a penetration depth of from 100 to 200 μm. In a further preferred embodiment, 60% by weight, preferably 80% by weight, based on the total amount of active metal, is present in the shell of the catalyst to a penetration depth of 150 μm. The abovementioned data are determined by means of SEM (scanning electron microscopy) EPMA (electron probe microanalysis)-EDXS (energy dispersive X-ray spectroscopy) and are mean values. To determine the penetration depth of the active metal particles, a number of catalyst particles (e.g. 3, 4 or 5) are cut and ground perpendicular to the extrudate axis (when the catalyst is in the form of extrudates). The profiles of the active metal/Si concentration ratios are then determined by means of line scans. On each measurement line, a number, for example from 15 to 20, measurement points at equal intervals are measured; the size of the measurement spot is about 10 μm*10 μm. After integration of the amount of active metal over the depth, the frequency of the active metal in a zone can be determined.

Very particular preference is given to the amount of active metal, based on the concentration ratio of active metal to Si, on the surface of the coated catalyst determined by means of SEM EPMA-EDXS being from 2 to 25%, preferably from 4 to 10%, particularly preferably from 4 to 6%. The surface analysis is carried out by means of analyses of regions having dimensions of 800 μm×2000 μm at an information depth of about 2 μm. The elemental composition is determined in % by weight (normalized to 100%). The mean concentration ratio (active metal/Si) is determined over 10 measurement regions.

For the purposes of the present invention, the surface of the coated catalyst is the outer shell of the catalyst to a penetration depth of about 2 μm. This penetration depth corresponds to the information depth in the abovementioned surface analysis.

Very particular preference is given to a coated catalyst in which the amount of active metal, based on the weight ratio of active metal to Si (weight/weight in %), on the surface of the coated catalyst is from 4 to 6%, at a penetration depth of 50 μm is from 1.5 to 3% and in a penetration depth range from 50 to 150 μm is from 0.5 to 2%, determined by means of SEM EPMA (EDXS). The values specified are mean values.

Furthermore, the size of the active metal particles preferably decreases with increasing penetration depth, determined by means of (FEG)-TEM analysis.

The active metal is preferably present either partly or completely in crystalline form in the coated catalyst. In preferred cases, very finely crystalline active metal can be detected in the shell of the coated catalyst by means of SAD (selected area diffraction) or XRD (X-ray diffraction).

The coated catalyst can further comprise alkaline earth metal ions (($M^{2+}$)), i.e. M=Be, Mg, Ca, Sr and/or Ba, in particular Mg and/or Ca, very particularly preferably Mg. The content of alkaline earth metal ion(s) ($M^{2+}$) in the catalyst is preferably from 0.01 to 1% by weight, in particular from 0.05 to 0.5% by weight, very particularly preferably from 0.1 to 0.25% by weight, in each case based on the weight of silicon dioxide support material.

An important constituent of catalyst variant III is the support material based on silicon dioxide, in general amorphous silicon dioxide. In this context, the term "amorphous" means that the proportion of crystalline silicon dioxide phases is less than 10% by weight of the support material. However, the support materials used for preparing the catalysts can have superstructures formed by a regular arrangement of pores in the support material.

As support materials, it is basically possible to use amorphous types of silicon dioxide which comprise at least 90% by weight of silicon dioxide, with the remaining 10% by weight, preferably not more than 5% by weight, of the support material also being able to be another oxidic material, e.g. MgO, CaO, $TiO_2$, $ZrO_2$, $Fe_2O_3$ and/or alkali metal oxide.

In a preferred embodiment of the invention, the support material is halogen-free, in particular chlorine-free, i.e. the halogen content of the support material is less than 500 ppm by weight, e.g. in the range from 0 to 400 ppm by weight. Preference is thus given to a coated catalyst which comprises less than 0.05% by weight of halide (determined by ion chromatography), based on the total weight of the catalyst.

Preference is given to support materials which have a specific surface area in the range from 30 to 700 m²/g, preferably from 30 to 450 m²/g (BET surface area in accordance with DIN 66131).

Suitable amorphous support materials based on silicon dioxide are known to those skilled in the art and are commercially available (cf., for example, O. W. Flörke, "Silica" in Ullmann's Encyclopedia of Industrial Chemistry 6th Edition on CD-ROM). They can be of natural origin or can have been produced synthetically. Examples of suitable amorphous support materials based on silicon dioxide are silica gels, kieselguhr, pyrogenic silicas and precipitated silicas. In a preferred embodiment of the invention, the catalysts have silica gels as support materials.

Depending on the embodiment of the invention, the support material can have a different form. If the process in which the coated catalysts are used is a suspension process, the support material is usually used in the form of a fine powder for producing the catalysts. The powder preferably has particle sizes in the range from 1 to 200 μm, in particular from 1 to 100 μm. When the coated catalyst according to the invention is used in fixed beds of catalyst, it is usual to use shaped bodies composed of the support material which can be obtained, for example, by extrusion, ram extrusion or tableting and can, for example, have the shape of spheres, pellets, cylinders, extrudates, rings or hollow cylinders, stars and the like. The dimensions of the shaped bodies are usually in the range from 0.5 mm to 25 mm. Catalyst extrudates having extrudate diameters of from 1.0 to 5 mm and extrudate lengths of from 2 to 25 mm are frequently used. In general, higher activities can be achieved when using relatively small extrudates, but these often do not have sufficient mechanical stability in the hydrogenation process. Very particular preference is therefore given to using extrudates having extrudate diameters in the range from 1.5 to 3 mm.

Preferred Processes for the Hydrogenation of Phthalates Using the Catalysts

The above-described catalysts (catalyst variants I, II and III and the subvariants mentioned) are preferably used as hydrogenation catalyst. They are suitable, in particular, for the hydrogenation of a carbocyclic aromatic group to the corresponding carbocyclic aliphatic group. Here, complete hydrogenation of the aromatic group particularly preferably occurs. According to the invention, these are phthalates, with the expression complete hydrogenation referring to a conversion of the compound to be hydrogenated of generally >98%, preferably >99%, particularly preferably >99.5% very particularly preferably >99.9%, in particular >99.99% and especially >99.995%.

When the catalysts I, II and/or III are used for the hydrogenation of aromatic dicarboxylic esters, in particular phthalic esters to the corresponding dialkyl cyclohexanedicarboxylates, the typical specifications which require a residual content of the aromatic dicarboxylic ester, in particular residual phthalic ester content, of <100 ppm (corresponding to a conversion of >99.99%) are thus likewise adhered to. As indicated, the conversion in a hydrogenation of aromatic dicarboxylic esters, in particular phthalic esters, using the coated catalyst according to the invention is preferably >99.995%.

The present patent application therefore also provides a process for the hydrogenation of phthalates to the corresponding cyclohexanedicarboxylic acid derivatives.

The carbocyclic aromatic group is preferably part of an aromatic hydrocarbon which has the following general formula:

where the symbols have the following meanings:
A is phenylene $C_6H_4$
n is 2
B is COOR, where R is H, alkyl substituted alkyl cycloalkyl, substituted cycloalkyl, aryl or substituted aryl; preferably H or $C_{1-20}$-alkyl.

For the purposes of the present patent application, the term alkyl refers, unless indicated otherwise, to branched or linear, saturated acyclic hydrocarbon radicals. The alkyl radicals generally have from 1 to 20 carbon atoms.

In the abovementioned group COOR, R is H or branched or linear alkyl preferably H or $C_{1-12}$-alkyl. Greater preference is given to $C_{4-10}$-alkyl groups, particularly preferably $C_{8-10}$-alkyl groups. These can be branched or unbranched and are preferably branched. Alkyl groups having more than three carbon atoms can be isomer mixtures of various alkyl groups having the same number of carbon atoms. An example is a $C_9$-alkyl group, which can be an isononyl group, i.e. an isomer mixture of various $C_9$-alkyl groups. The same applies to, for example, a $C_8$-alkyl group. Such isomer mixtures are obtained from the alcohols corresponding to the alkyl groups which, owing to their method of production which is known to those skilled in the art, are obtained as isomer mixtures.

For the purposes of the present patent application, the term cycloalkyl refers to saturated cyclic nonaromatic hydrocarbon radicals which are made up of a single ring or a plurality of fused rings. Suitable cycloalkyl radicals are, for example, cyclopentyl, cyclohexyl, cyclooctyl, bicyclooctyl, etc. The cycloalkyl radicals preferably have from 3 to 50 carbon atoms, particularly preferably from 3 to 20 carbon atoms, very particularly preferably from 3 to 8 carbon atoms and in particular from 3 to 6 carbon atoms.

Substituted cycloalkyl radicals are those in which one or more hydrogen atoms of any particular carbon atom of the carbon ring are replaced by another group. Such other groups are, for example, halogen, alkyl, alkenyl, alkynyl, substituted alkyl, substituted alkenyl, substituted alkynyl, aryl, substituted aryl, cycloalkyl, cycloalkenyl, substituted cycloalkyl, substituted cycloalkenyl, an aliphatic heterocyclic radical, a substituted aliphatic heterocyclic radical, heteroaryl, substituted heteroaryl, alkoxy, aryloxy, boryl, phosphino, amino, silyl and combinations thereof. Examples of substituted cycloalkyl and cycloalkenyl radicals are 4-dimethylaminocyclohexyl, 4,5-dibromocyclohept-4-enyl etc.

In a further preferred embodiment of the hydrogenation process, the aromatic hydrocarbon is selected from the group consisting of phthalic acid (benzene-1,2-dicarboxylic acid) and its isomers benzene-1,3-dicarboxylic acid (isophthalic acid) and benzene-1,4-dicarboxylic acid (terephthalic acid) and $C_1$-$C_{20}$-alkyl esters of phthalic acid, isophthalic acid and terephthalic acid, preferably $C_{1-12}$-alkyl esters of phthalic acid, isophthalic acid and terephthalic acid, with the $C_{1-12}$-alkyl radicals being able to be linear or branched, e.g. dimethyl phthalate, dimethyl isophthalate, dimethyl terephthalate, di-2-propylheptyl phthalate, di-2-propylheptyl isophthalate, di-2-propylheptyl terephthalate, di-2-ethylhexyl phthalate, di-2-ethylhexyl isophthalate, di-2-ethylhexyl terephthalate, dioctyl phthalate, dioctyl isophthalate, dioctyl terephthalate, diisononyl phthalate, diisononyl isophthalate, diisononyl terephthalate. Preference is thus given, in the process of the invention, to hydrogenating aromatic carboxylic acids such as phthalic acid, isophthalic acid and terephthalic acid to cycloaliphatic carboxylic acids, and the corresponding $C_{1-12}$-alkyl esters of phthalic acid, isophthalic acid and terephthalic acid to the corresponding aliphatic carboxylic esters, for example dimethyl phthalate to dimethyl cyclohexanedicarboxylate, di-2-propylheptyl phthalate to di-2-propylheptyl cyclohexanedicarboxylate, di-2-ethylhexyl phthalate to di-2-ethylhexyl cyclohexanedicarboxylate, dioctyl phthalate to dioctyl cyclohexanedicarboxylate and diisononyl phthalate to diisononyl cyclohexanedicarboxylate. For the purposes of the present invention, phthalates are particularly preferred.

The phthalates according to the invention are specified below.

In the preparation of diisononyl phthalate, the isononyl radicals originate from an esterification reaction with isononanols which is known per se. Preference is here given to using isononanols (C9-alcohols) which have a degree of branching (ISO index) of generally from 0.10 to 4, preferably from 0.5 to 3, particularly preferably from 0.8 to 2 and in particular from 1 to 1.5, i.e. the respective alcohols are generally mixtures of various isomers. Very particular preference is given to using C9-alcohol mixtures having an ISO index of from 1 to 1.5, in particular nonanol mixtures having an ISO index of 1.25 or 1.6.

The ISO index is a dimensionless parameter which is determined by means of gas chromatography.

It is calculated from the degree of branching of the components comprised in the alcohol mixture and the amount of the corresponding components (determined by means of gas chromatography). The precise method of calculation is known to those skilled in the art.

The isononanols are prepared by processes known to those skilled in the art. Particular preference is given to using a nonanol mixture in which from 0 to 20% by weight, preferably from 0.5 to 18% by weight, particularly preferably from 6 to 16% by weight, of the nonanol mixture has no branches, from 5 to 90% by weight, preferably from 10 to 80% by weight, particularly preferably from 45 to 75% by weight, has one branch, from 5 to 70% by weight, preferably from 10 to 60% by weight, particularly preferably from 15 to 35% by weight, has two branches, from 0 to 10% by weight, preferably from 0 to 8% by weight, particularly preferably from 0 to 4% by weight, has three branches and from 0 to 40% by weight, preferably from 0.1 to 30% by weight, particularly preferably from 0.5 to 6.5% by weight, is made up of other components. Other components are generally nonanols having more than three branches, decanols or octanols, with the sum of the components mentioned being 100% by weight.

A particularly preferred embodiment of a nonanol mixture which is used for preparing the preferred cyclohexanepolycarboxylic acid derivatives has the following composition:

from 1.73 to 3.73% by weight, preferably from 1.93 to 3.53% by weight, particularly preferably from 2.23 to 3.23% by weight, of 3-ethyl-6-methylhexanol;

from 0.38 to 1.38% by weight, preferably from 0.48 to 1.28% by weight, particularly preferably from 0.58 to 1.18% by weight, of 2,6-dimethylheptanol;

from 2.78 to 4.78% by weight, preferably from 2.98 to 4.58% by weight, particularly preferably from 3.28 to 4.28% by weight, of 3,5-dimethylheptanol;

from 6.30 to 16.30% by weight, preferably from 7.30 to 15.30% by weight, particularly preferably from 8.30 to 14.30% by weight, of 3,6-dimethylheptanol;

from 5.74 to 11.74% by weight, preferably from 6.24 to 11.24% by weight, particularly preferably from 6.74 to 10.74% by weight, of 4,6-dimethylheptanol;

from 1.64 to 3.64% by weight, preferably from 1.84 to 3.44% by weight, particularly preferably from 2.14 to 3.14% by weight, of 3,4,5-trimethylhexanol;

from 1.47 to 5.47% by weight, preferably from 1.97 to 4.97% by weight, particularly preferably from 2.47 to 4.47% by weight, of 3,4,5-trimethyl hexanol, 3-methyl-4-ethylhexanol and 3-ethyl-4-methylhexanol;

from 4.00 to 10.00% by weight, preferably from 4.50 to 9.50% by weight, particularly preferably from 5.00 to 9.00% by weight, of 3,4-dimethylheptanol;

from 0.99 to 2.99% by weight, preferably from 1.19 to 2.79% by weight, particularly preferably from 1.49 to 2.49% by weight, of 4-ethyl-5-methylhexanol and 3-ethylheptanol;

from 2.45 to 8.45% by weight, preferably from 2.95 to 7.95% by weight, particularly preferably from 3.45 to 7.45% by weight, of 4,5-dimethylheptanol and 3-methyloctanol;

from 1.21 to 5.21% by weight, preferably from 1.71 to 4.71% by weight, particularly preferably from 2.21 to 4.21% by weight, of 4,5-dimethylheptanol;

from 1.55 to 5.55% by weight, preferably from 2.05 to 5.05% by weight, particularly preferably from 2.55 to 4.55% by weight, of 5,6-dimethylheptanol;

from 1.63 to 3.63% by weight, preferably from 1.83 to 3.43% by weight, particularly preferably from 2.13 to 3.13% by weight, of 4-methyloctanol;

from 0.98 to 2.98% by weight, preferably from 1.18 to 2.78% by weight, particularly preferably from 1.48 to 2.48% by weight, of 5-methyloctanol;

from 0.70 to 2.70% by weight, preferably from 0.90 to 2.50% by weight, particularly preferably from 1.20 to 2.20% by weight, of 3,6,6-trimethylhexanol;

from 1.96 to 3.96% by weight, preferably from 2.16 to 3.76% by weight, particularly preferably from 2.46 to 3.46% by weight, of 7-methyloctanol;

from 1.24 to 3.24% by weight, preferably from 1.44 to 3.04% by weight, particularly preferably from 1.74 to 2.74% by weight, of 6-methyloctanol;

from 0.1 to 3% by weight, preferably from 0.2 to 2% by weight, particularly preferably from 0.3 to 1% by weight, of n-nonanol;

from 25 to 35% by weight, preferably from 28 to 33% by weight, particularly preferably from 29 to 32% by weight, of other alcohols having 9 and 10 carbon atoms, with the total sum of the components specified being 100% by weight.

A further particularly preferred embodiment of a nonanol mixture used for preparing preferred cyclohexanepolycarboxylic acid derivatives has the following composition:

from 6.0 to 16.0% by weight, preferably from 7.0 to 15.0% by weight, particularly preferably from 8.0 to 14.0% by weight, of n-nonanol;

from 12.8 to 28.8% by weight, preferably from 14.8 to 26.8% by weight, particularly preferably from 15.8 to 25.8% by weight, of 6-methyloctanol;

from 12.5 to 28.8% by weight, preferably from 14.5 to 26.5% by weight, particularly preferably from 15.5 to 25.5% by weight, of 4-methyloctanol;

from 3.3 to 7.3% by weight, preferably from 3.8 to 6.8% by weight, particularly preferably from 4.3 to 6.3% by weight, of 2-methyloctanol;

from 5.7 to 11.7% by weight, preferably from 6.3 to 11.3% by weight, particularly preferably from 6.7 to 10.7% by weight, of 3-ethylheptanol;

from 1.9 to 3.9% by weight, preferably from 2.1 to 3.7% by weight, particularly preferably from 2.4 to 3.4% by weight, of 2-ethylheptanol;

from 1.7 to 3.7% by weight, preferably from 1.9 to 3.5% by weight, particularly preferably from 2.2 to 3.2% by weight, of 2-propylhexanol;

from 3.2 to 9.2% by weight, preferably from 3.7 to 8.7% by weight, particularly preferably from 4.2 to 8.2% by weight, of 3,5-dimethylheptanol;

from 6.0 to 16.0% by weight, preferably from 7.0 to 15.0% by weight, particularly preferably from 8.0 to 14.0% by weight, of 2,5-dimethylheptanol;

from 1.8 to 3.8% by weight, preferably from 2.0 to 3.6% by weight, particularly preferably from 2.3 to 3.3% by weight, of 2,3-dimethylheptanol;

from 0.6 to 2.6% by weight, preferably from 0.8 to 2.4% by weight, particularly preferably from 1.1 to 2.1% by weight, of 3-ethyl-4-methylhexanol;

from 2.0 to 4.0% by weight, preferably from 2.2 to 3.8% by weight, particularly preferably from 2.5 to 3.5% by weight, of 2-ethyl-4-methylhexanol;

from 0.5 to 6.5% by weight, preferably from 1.5 to 6% by weight, particularly preferably from 1.5 to 5.5% by weight, of other alcohols having 9 carbon atoms;

with the total sum of the components specified being 100% by weight.

For the purposes of the present invention, the terms "phthalates", "isophthalates" and "terephthalates" comprise both the free acids and the esters mentioned.

The hydrogenation process can be carried out in the liquid phase or in the gas phase. The hydrogenation process of the invention is preferably carried out in the liquid phase.

The hydrogenation process can be carried out in the absence of a solvent or diluent or in the presence of a solvent or diluent, i.e. it is not necessary to carry out the hydrogenation in solution.

As solvent or diluent, it is possible to use any suitable solvent or diluent. Possible solvents or diluents are in principle those which are able to dissolve the organic compound to be hydrogenated, preferably completely, or mixed completely with this and are inert under the hydrogenation conditions, i.e. are not hydrogenated.

Examples of suitable solvents are cyclic and acyclic ethers, e.g. tetrahydrofuran, dioxane, methyl tert-butyl ether, dimethoxyethane, dimethoxypropane, dimethyldiethylene glycol, aliphatic alcohols such as methanol, ethanol, n-propanol or isopropanol, n-butanol, 2-butanol, isobutanol or tert-butanol, carboxylic esters such as methyl acetate, ethyl acetate, propyl acetate or butyl acetate, and also aliphatic ether alcohols such as methoxypropanol and cycloaliphatic compounds such as cyclohexane, methylcyclohexane and dimethylcyclohexane.

The amount of solvent or diluent used is not subject to any particular restrictions and can be selected freely according to requirements, but preference is given to amounts which lead to a from 3 to 70% strength by weight solution of the organic compound intended for hydrogenation. The use of a diluent is advantageous in order to avoid excessive evolution of heat in the hydrogenation process. Excessive evolution of heat can lead to deactivation of the catalyst and is therefore undesirable. Careful temperature control is therefore advantageous in the hydrogenation process. Suitable hydrogenation temperatures are mentioned below.

When a solvent is used, particular preference is given to using, for the purposes of the invention, the product formed in the hydrogenation, i.e. preferably the respective cycloaliphatic(s), as solvent, if appropriate together with other solvents or diluents. In any case, part of the product formed in the process can be mixed into the aromatics still to be hydrogenated. In the hydrogenation of phthalates, the corresponding dialkyl cyclohexanedicarboxylates are preferably used as solvents.

Based on the weight of the phthalates, isophthalates and terephthalates intended for hydrogenation, preference is given to mixing in from 1 to 30 times, particularly preferably from 5 to 20 times, in particular from 5 to 10 times, the amount of the product to be formed as solvent or diluent.

The actual hydrogenation is usually carried out by bringing the organic compound as liquid phase or gaseous phase, preferably as liquid phase, into contact with the catalyst in the presence of hydrogen. The liquid phase can be passed over a catalyst suspension (suspension process) or a fixed bed of catalyst (fixed-bed process).

The hydrogenation can be carried out either continuously or batchwise, with a continuous process being preferred. The process is preferably carried out in trickle reactors or in the flooded mode of operation according to the fixed-bed mode of operation. The hydrogen can be passed over the catalyst either in concurrent with the solution of the starting material to be hydrogenated or in countercurrent.

Suitable apparatuses for carrying out a hydrogenation over a moving bed or fixed bed of catalyst are known from the prior art, e.g. from Ullmanns Enzyklopädie der Technischen Chemie, 4th edition, volume 13, p. 135 ff., and from P. N. Rylander, "Hydrogenation and Dehydrogenation" in Ullmann's Encyclopedia of Industrial Chemistry, 5th ed. on CD-ROM.

The hydrogenation can be carried out either under hydrogen at atmospheric pressure or under an increased hydrogen pressure, e.g. at an absolute hydrogen pressure of at least 1.1 bar, preferably at least 2 bar. In general, the absolute hydrogen pressure will not exceed a value of 325 bar and preferably 300 bar. The absolute hydrogen pressure is preferably in the range from 1.1 to 300 bar.

In the process of the invention, the reaction temperatures are generally at least 30° C. and will frequently not exceed a value of 250° C. The hydrogenation process is preferably carried out at temperatures in the range from 50 to 200° C., particularly preferably from 70 to 180° C., and very particularly preferably in the range from 80 to 160° C. The hydrogenation of phthalates is most preferably carried out, for example, at temperatures in the range from 75° C. to 170° C., in particular from 80° C. to 160° C.

Possible reaction gases include not only hydrogen but also hydrogen-comprising gases which comprise no catalyst poisons such as carbon monoxide or sulfur-comprising gases such as $H_2S$ or COS, e.g. mixtures of hydrogen with inert gases such as nitrogen or offgases from a reformer which usually further comprise volatile hydrocarbons. Preference is given to using pure hydrogen (purity=99.9% by volume particularly =99.95% by volume, in particular =99.99% by volume).

Owing to the high catalyst activity, comparatively small amounts of catalyst based on the starting material used are required. Thus, in a batch suspension process, preference is given to using less than 5 mol %, e.g. from 0.2 mol % to 2 mol %, of active metal, based on 1 mol of starting material. In the case of a continuous hydrogenation process, the starting material to be hydrogenated is usually passed over the catalyst at a space velocity of from 0.05 to 3 kg/(l(catalyst)·h), in particular from 0.15 to 2 kg/(l(catalyst)·h).

Particularly Preferred Hydrogenation Processes

The hydrogenation according to the invention of phthalates isophthalates and terephthalates, preferably phthalates, comprising a regeneration is generally carried out at a temperature of from 50° C. to 250° C., preferably from 70° C. to 220° C. The pressure is generally ≥10 bar.

In the present process, preference is given to hydrogenating diisononyl phthalate at a pressure in the range from about 200 to about 250 bar to form diisononyl cyclohexanedicarboxylate.

The hydrogenation can generally be carried out in the suspension or fixed-bed mode, with the fixed-bed mode being preferred. The hydrogenation process is particularly preferably carried out with recirculation of liquid, with the heat of hydrogenation being able to be removed by means of a heat exchanger and utilized. The feed/recycle ratio when the hydrogenation process is carried out with recirculation of liquid is generally from 1:5 to 1:40, preferably from 1:10 to 1:30.

To achieve complete conversion, an after-reaction of the hydrogenation product mixture can be carried out. For this purpose, the hydrogenation product mixture can, subsequent to the hydrogenation process, be passed in the gas phase or in the liquid phase in a single pass through a downstream reactor. In the case of a liquid-phase hydrogenation, the reactor can be operated in the downflow mode or in a flooded state. The reactor is charged with the catalyst according to the invention or with another catalyst known to those skilled in the art.

Regeneration Step

In hydrogenation processes in which the catalysts described above are used, deactivation is observed after a period of operation of the catalyst. Such a deactivated ruthenium catalyst can be brought back to the state of the original activity by flushing. The activity can be restored to >90%, preferably >95%, more preferably >98%, in particular >99%, most preferably >99.5%, of the original value. The deactivation is attributed to traces or residues of water adsorbed on the catalyst. This can surprisingly be reversed by flushing with inert gas. The regeneration method of the invention can thus also be referred to as drying of the catalyst or removal of water from this.

Flushing means that the catalyst is brought into contact with inert gas. Normally, the inert gas is then passed over the catalyst by means of suitable constructional measures known to those skilled in the art.

The flushing with inert gas is carried out at a temperature of from about 10 to 350° C., preferably from about 50 to 250° C., particularly preferably from about 70 to 180° C., most preferably from about 80 to 130° C.

The pressures applied during flushing are from 0.5 to 5 bar, preferably from 0.8 to 2 bar, in particular from 0.9 to 1.5 bar.

According to the invention, the treatment of the catalyst is preferably carried out using an inert gas. Preferred inert gases comprise nitrogen, carbon dioxide, helium, argon, neon and mixtures thereof. Nitrogen is most preferred.

In a particular embodiment of the invention, the inventive method of regeneration is carried out without removal of the catalyst in the same reactor in which the hydrogenation has taken place. The flushing of the catalyst according to the present invention is particularly advantageously carried out at temperatures and pressures in the reactor which correspond to or are similar to those in the hydrogenation reaction, resulting in only a very brief interruption of the reaction process.

According to the present invention, the flushing with inert gas is carried out at a volume flow of from 20 to 200 standard l/h, preferably at a volume flow of from 50 to 200 standard l/h per liter of catalyst.

The flushing with inert gas is preferably carried out for a time of from 10 to 50 hours, particularly preferably from 10 to 20 hours. For example, the calculated drying time of the catalyst bed of an industrial production plant having an assumed moisture content of 2 or 5% by weight is approximately 18 or 30 hours, respectively. The flushing according to the method of the invention can be carried out either in a downward direction (downflow mode) or in an upward direction (upflow mode).

The present invention further provides an integrated process for the hydrogenation of phthalates, isophthalates and terephthalates and the corresponding acids, preferably phthalates, in the presence of a ruthenium catalyst having a catalyst regeneration step, which comprises the following steps:

(a) provision of at least one phthalate, isophthalate or terephthalate and a ruthenium catalyst;
(b) hydrogenation of the aromatic compound used by contact with hydrogen in the presence of the ruthenium catalyst until the catalyst has a reduced hydrogenation activity,
(c) regeneration of the catalyst by flushing with inert gas,
(d) if appropriate, repetition of the steps (a) to (c).

The hydrogen used according to the invention preferably comprises no damaging catalyst poisons such as CO. For example, reformer gases can be used. Preference is given to using pure hydrogen as hydrogenation gas.

The method of the invention is also suitable for drying catalysts which have absorbed water during various procedures such as maintenance or storage.

The invention accordingly provides a method of drying and/or reactivating and/or regenerating a catalyst comprising ruthenium on a support material, in which the catalyst is treated with an inert gas. After this treatment, the catalyst has a higher catalytic activity than before.

The invention is illustrated by the following examples.

FIG. 1 shows a flow diagram of the preparation of diisononyl cyclohexane-1,2-dicarboxylate (cf. Example 2)

EXAMPLE OF THE PRODUCTION OF THE RUTHENIUM CATALYST

A mesoporous/macroporous aluminum oxide support in the form of 3-5 mm spheres having a total volume of 0.44 cm$^3$/g, with 0.09 cm$^3$/g (20% of the total pore volume) being formed by pores having a diameter in the range from 50 nm to 10 000 nm and 0.35 cm$^3$/g (80% of the total pore volume) being formed by pores having a diameter in the range from 2 nm to 50 nm, a mean pore diameter in the region of 11 nm and a surface area of 286 m$^2$/g was impregnated with an aqueous ruthenium(III) nitrate solution. The volume of solution taken up during impregnation corresponded approximately to the pore volume of the support used. The support impregnated with the ruthenium(III) nitrate solution was subsequently dried at 120° C. and activated (reduced) in a stream of hydrogen at 200° C. The catalyst produced in this way comprised 0.5% by weight of ruthenium, based on the weight of the catalyst. The ruthenium surface area was 0.72 m$^2$/g, and the ratio of ruthenium surface area to support surface area was 0.0027.

EXAMPLE 1

Sorption Studies

The affinity of the catalyst for water was determined by means of measurements of the sorption of water vapor on the catalyst produced as described above (0.5% Ru/$\gamma$—Al$_2$O$_3$).

It was found that the catalyst sorbs an amount of water of 5% even at relatively low vapor pressures of 30%. If only traces of water are present in the reactor or in the starting materials, this water can be sorbed on the catalyst.

EXAMPLE 2

Comparison with and without Drying

In the hydrogenation of diisononyl phthalate to DINCH, it is found that after operation for 3 months, the residual phthalate content of <100 ppm can only be achieved by means of a gradual reduction in the space velocity over the catalyst (=reduction in the feed rate of DINP). Temperature and pressure increases lead to no improvement. The experimental plant is described below:

The plant comprises two reactors 1 and 2 connected in series (FIG. 1). The heat of reaction is taken off from the recirculation circuit of reactor 1 by cooling. Both reactors 1 and 2 (denoted by 1 and 2 for short in the FIGURE) are operated in the downflow mode. A is the introduction of DINP; B is the introduction of H$_2$.

Reactor size and catalyst volume are shown in Table 1 below.

|  | Reactor 1 | Reactor 2 |
| --- | --- | --- |
| Catalyst volume | 2.7 l | 0.34 l |
| Reactor dimensions | 45 × 2000 mm | 22 × 1500 mm |
| Height of the active bed | 1.86 m | 1.14 m |

To carry out drying, the liquid is emptied from the reactors 1 and 2 and 13 standard m$^3$/h of nitrogen which has been heated to 110° C. are passed through the two reactors for 7 days. This leads to removal of the water adsorbed on the catalyst. After resumption of operation, the activity of the catalyst is significantly increased. The amount produced can be doubled, and the residual phthalate content is <100 ppm. The experiments after an operating time of 3 months both before drying and after drying are shown in Table 2.

TABLE 2

|  | DINP feed [kg/h] | Temp. in reactor 1 [° C.] | Pressure in reactor 1 [bar] | Temp. in reactor 2 [° C.] | Pressure in reactor 2 [bar] | Production of DINCH [kg/h] | Residual aromatics [ppm] |
| --- | --- | --- | --- | --- | --- | --- | --- |
| before drying | 0.3 | 121 | 264 | 136 | 263 | 0.3 | 95 |
| after drying | 0.52 | 121 | 265 | 142 | 264 | 0.52 | 50 |

The invention claimed is:

1. An integrated process for the hydrogenation of phthalates, isophthalates or terephthalates in the presence of a ruthenium catalyst consisting of:
   (a) providing at least one phthalate, isophthalate or terephthalate and a ruthenium catalyst;
   (b) hydrogenating the at least one phthalate, isophthalate or terephthalate by contact with hydrogen in the presence of the ruthenium catalyst until the catalyst has a reduced hydrogenation activity, and
   (c) flushing the catalyst with inert gas
   until the original activity or part of the original activity has been attained.

2. The method according to claim 1, wherein the flushing with inert gas is carried out at a temperature of from 10 to 350° C.

3. The method according to claim 2, wherein the pressure applied during flushing is from 0.5 to 5 bar.

4. The method according to claim 2, wherein the inert gas is selected from among nitrogen, carbon dioxide, helium, argon, neon and mixtures thereof.

5. The method according to claim 2, wherein the flushing with inert gas is carried out at a volume flow of from 20 to 200 standard l/h per liter of catalyst.

6. The method according to claim 2, wherein flushing with inert gas is carried out for a time of from 10 to 50 hours.

7. The method according to claim 1, wherein the pressure applied during flushing is from 0.5 to 5 bar.

8. The method according to claim 7, wherein the inert gas is selected from among nitrogen, carbon dioxide, helium, argon, neon and mixtures thereof.

9. The method according to claim 7, wherein the flushing with inert gas is carried out at a volume flow of from 20 to 200 standard l/h per liter of catalyst.

10. The method according to claim 1, wherein the inert gas is selected from among nitrogen, carbon dioxide, helium, argon, neon and mixtures thereof.

11. The method according to claim 10, wherein the flushing with inert gas is carried out at a volume flow of from 20 to 200 standard l/h per liter of catalyst.

12. The method according to claim 1, wherein the flushing with inert gas is carried out at a volume flow of from 20 to 200 standard l/h per liter of catalyst.

13. The method according to claim 1, wherein flushing with inert gas is carried out for a time of from 10 to 50 hours.

14. The method according to claim 1, wherein the flusching step is carried out until an activity of >90% of the original value is attained.

15. The method according to claim 1, wherein the ruthenium catalyst is selected from among the following groups:
  a) catalyst comprising, as active metal, ruthenium alone or ruthenium together with at least one metal of transition group I, VII or VIII of the Periodic Table of the Elements in an amount of from 0.01 to 30% by weight, based on the total weight of the catalyst, applied to a support, wherein from 10 to 50% of the pore volume of the support is formed by macropores having a pore diameter in the range from 50 nm to 10 000 nm and from 50 to 90% of the pore volume of the support being formed by mesopores having a pore diameter in the range from 2 to 50 nm, with the sum of the pore volumes being 100%, and
  b) coated catalyst comprising, as active metal, ruthenium alone or ruthenium together with at least one further metal of transition group IB, VIIB or VIII of the Periodic Table of the Elements applied to a support comprising silicon dioxide as support material, wherein the amount of active metal is <1% by weight, based on the total weight of the catalyst, and at least 60% by weight of the active metal is present in the shell of the catalyst to a penetration depth of 200 μm, determined by means of SEM-EPMA (EDXS).

16. The method according to claim 1, wherein the catalyst is a catalyst comprising, as active metal, ruthenium alone or ruthenium together with at least one metal of transition group I, VII or VIII of the Periodic Table of the Elements in an amount of from 0.01 to 30% by weight, based on the total weight of the catalyst, applied to a support, wherein from 10 to 50% of the pore volume of the support is formed by macropores having a pore diameter in the range from 50 nm to 10 000 nm and from 50 to 90% of the pore volume of the support being formed by mesopores having a pore diameter in the range from 2 to 50 nm, with the sum of the pore volumes being 100%, and the at least one metal of transition group I, VII or VIII of the Periodic Table of the Elements is platinum, copper, rhenium, cobalt, nickel or a mixture of two or more thereof.

17. The method according to claim 1, wherein the catalyst is a catalyst comprising, as active metal, ruthenium alone or ruthenium together with at least one metal of transition group I, VII or VIII of the Periodic Table in an amount of from 0.01 to 30% by weight, based on the total weight of the catalyst, applied to a support, wherein from 10 to 50% of the pore volume of the support is formed by macropores having a pore diameter in the range from 50 nm to 10 000 nm and from 50 to 90% of the pore volume of the support being formed by mesopores having a pore diameter in the range from 2 to 50 nm, with the sum of the pore volumes being 100%, and the support is activated carbon, silicon carbide, aluminum oxide, titanium oxide, zirconium oxide, magnesium oxide, zinc oxide or a mixture of two or more thereof.

18. The method according to claim 1, wherein the catalyst is a catalyst comprising, as active metal, ruthenium alone or ruthenium together with at least one further metal of transition group IB, VIIB or VIII of the Periodic Table of the Elements applied to a support comprising silicon dioxide as support material, wherein the amount of active metal is <1% by weight, based on the total weight of the catalyst, and at least 60% by weight of the active metal is present in the shell of the catalyst to a penetration depth of 200 μm, determined by means of SEM-EPMA (EDXS) and the at least one metal of transition group I, VII or VIII of the Periodic Table is platinum, copper, rhenium, cobalt, nickel or a mixture of two or more thereof.

19. The method according to claim 1, wherein diisononyl phthalate is converted into diisononyl cyclohexanedicarboxylate.

* * * * *